United States Patent
Nielsen et al.

(10) Patent No.: US 6,764,474 B2
(45) Date of Patent: *Jul. 20, 2004

(54) OSTOMY APPLIANCE

(75) Inventors: Inger Mann Nielsen, Frederiksberg (DK); Eskil Hoejland Olsen, Klampenborg (DK); Laila Busk Gothjaelpsen, Hvidovre (DK); Danuta Ciok, Nivaa (DK); Carsten Sletten, Copenhagen (DK); Anders Christian Nielsen, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/091,648

(22) PCT Filed: Oct. 22, 1997

(86) PCT No.: PCT/DK97/00464

§ 371 (c)(1),
(2), (4) Date: Jun. 22, 1998

(87) PCT Pub. No.: WO98/17212

PCT Pub. Date: Apr. 30, 1998

(65) Prior Publication Data

US 2003/0004477 A1 Jan. 2, 2003

(30) Foreign Application Priority Data

| Oct. 22, 1996 | (DK) | 1166/96 |
| Apr. 30, 1997 | (DK) | 0488/97 |
| May 30, 1997 | (DK) | 0636/97 |
| May 26, 1997 | (DK) | 0598/97 |

(51) Int. Cl.[7] .................................................. A61F 5/44
(52) U.S. Cl. ..................................... 604/344; 604/336
(58) Field of Search ............................... 604/344, 336, 604/338

(56) References Cited

U.S. PATENT DOCUMENTS

| 4,095,599 | A | | 6/1978 | Simonet-Haibe |
| 4,367,732 | A | | 1/1983 | Poulsen et al. |
| 4,551,490 | A | | 11/1985 | Doyle et al. ................. 524/22 |
| 5,013,307 | A | * | 5/1991 | Broida ....................... 604/338 |
| 5,496,296 | A | * | 3/1996 | Holmberg ................... 604/336 |
| 6,312,415 | B1 | * | 11/2001 | Nielsen et al. .............. 604/342 |
| 6,332,879 | B1 | * | 12/2001 | Nielsen et al. .............. 604/344 |

FOREIGN PATENT DOCUMENTS

| DK | 147035 | | 12/1967 |
| EP | 0 686 381 | | 12/1995 |
| GB | 2 277 031 | | 10/1994 |
| GB | 2290974 | * | 1/1996 |
| GB | 2 290 974 | * | 1/1996 |
| WO | 9218074 | * | 10/1992 |
| WO | 92/18074 | | 10/1992 |
| WO | 9817212 | * | 4/1998 |
| WO | 9853771 | * | 12/1998 |
| WO | 9855057 | * | 12/1998 |

* cited by examiner

*Primary Examiner*—Karin Reichle
(74) *Attorney, Agent, or Firm*—Jacobson Holman PLLC

(57) ABSTRACT

An ostomy appliance comprising a body side member comprising an adhesive wafer or pad for securing the appliance to the user's skin, said wafer or pad having a hole for receiving a stoma, and an optionally separately exchangeable receiving member or bag secured to the body side ostomy member for receiving secretions from the ostomy, said ostomy appliance further comprising a separate sealing member disposed in the hole of the wafer or pad surrounding the stoma, said sealing member being of a hypo-allergenic adhesive and being in the form of a moldable mass or a ring.

8 Claims, 11 Drawing Sheets

OSTOMY APPLIANCE

BACKGROUND OF THE INVENTION

1. Field of the Invention

The present invention relates to an ostomy appliance, and a method for the use of a body member and a body side ostomy member

2. Description of the Related Art

In connection with surgery for a number of diseases in the gastrointestinal tract a consequence is, in many cases, that the colon, the ileum or the urethra is exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance.

When using one-piece appliances, the whole appliance, including the adhesive wafer or pad securing the appliance to the skin is removed and replaced by a fresh appliance. When using two-piece appliances, the body side ostomy member is left in place for several days, and only the receiving member or bag is replaced.

The service time of the body side ostomy member depends on the amount and aggressiveness of the exudates and of the tightness between the ostomy and the body side ostomy member.

In the known appliances it is necessary to change the body side member of two-piece appliance when the center part of the adhesive wafer or pad has been sufficiently deteriorated to allow access of the aggressive exudates to the skin surrounding the stoma, irrespective of the fact that the wafer as such has a much longer wearing time. The access of aggressive exudates to the skin causes skin problems.

Skin problems are common for persons having a stoma. Generally, about 40% have skin problems (Pearl et al. 1985 "Early local complications from intestinal stomas", Arch. Surg. 120; 1145–1147) and the frequency is especially high for persons having an urostomy or ileostomy. About 80% of the persons having an ileostomy have skin problems (Hellman, J. D., Lago, C. P. 1990 "Dermatologic complications in colostomy and ileostomy patients", International Journal of Dermatology, 29 (2); 129–133). The skin problems are most pronounced in a circular area about the stoma (½ inch from the stoma) (Hellman and Lago 1990).

Frequent changing of the body side member of a two-piece appliance or the frequent exchange of a one-piece appliance is undesirable due to the irritation of the skin and the quality of life may be improved and the nuisance of the wearing of an ostomy appliance reduced if the intervals between exchanging of the body side member can be increased.

It is known to place a ring on the skin before applying the body side member or to make a filling between the edge of the stoma and the shaped whole of the ostomy appliance in order to form a seal between the stoma and the ostomy appliance in order to alleviate the problems using a commercially available medical grade adhesive paste. Such pastes are, e.g., sold by Bristol-Myers Squibb under the trademark STOMA HESIVE® or by Coloplast under the trade mark COLOPLAST® Paste.

These pastes, however, do not have a composition which has sufficient cohesion to ensure safe removal thereof without leaving residues on the skin and, on the other hand, the pastes often are so sticky that they cannot easily be shaped using the finger without sticking to the finger.

A paste should have a composition which is sufficiently tacky to secure the appliance or skin barrier to the abdomen, yet have a cohesion ensuring safe removal thereof without leaving residues on the skin. On the other hand, the paste must not be so sticky that it cannot easily be shaped by a finger or hand without sticking to the finger or hand. Furthermore, the paste must show a sufficient elasticity in order to be able to follow the movements of the patient without slipping on the skin and should also show a great resistance to erosion caused by aggressive exudates from an ostomy.

WO 92/18074 discloses a device in a stoma bandage comprising a sealing ring filled with a fluid to be applied around a stoma, the sealing ring being flexibly adjustable and having a variable diameter by the pressure of said liquid being increased or decreased for adjustment to the stoma of a user in order to seal between the stoma and the bandage. The sealing ring may be made of a material such as latex functioning as a septum through which an injection needle can be inserted in order to supply or remove fluid, respectively.

In GB Patent Application No. GB 2 290 974 is disclosed an ostomy appliance wherein a body-side member is combined with a mouldable mass of non-hypoallergenic, non-memory putty-like adhesive, particularly based on hydrocolloid or hydrogel.

GB Patent Application No. GB 2 290 974 discloses a body-side ostomy member comprising a ring to which a bag-side coupling ring or a bag can be attached, the ring comprising a rib and a flange, the flange being mounted on a wafer of medical grade adhesive having a central hole of diameter at least 65% of the internal diameter of the ring. A mouldable mass of non-hypoallergenic, non-memory putty-like adhesive, particularly based on hydrocolloid or hydrogel, is disposed radially inward of the wafer so that it forms a protective mass surrounding the stoma. The mouldable mass has a thickness of 1.25–3 times that of the wafer and a central hole therein of a diameter no more than ⅟₁₀ th of the internal diameter of the ring. Both the medical grade adhesive and the mouldable adhesive are adhered to the skin.

European Patent application No. EP 0 686 381 discloses an ostomy appliance comprising a collection pouch and faceplate assembly including a flexible patch having a stoma-receiving opening, a first layer of skin friendly hydrocolloid-containing adhesive material along one side of the patch about the opening for securing said faceplate assembly to peristomal skin surfaces, and a second layer of relatively soft, easily deformable and extrudable, adhesive sealant material of a composition that is resistant to being dissolved or disintegrated by stomal fluids and that immediately surrounds the opening; the second layer being displaceable inwardly and axially into the opening for forming a stoma-engaging annular gasket to prevent stomal fluids from contacting the peristomal skin and the first adhesive layer.

The sealing ring disclosed in WO 92/18074 does not provide a safe seal against stomal liquids if not inflated to relatively high pressures which may cause irritation to the user.

The mouldable mass of non-hypoallergenic, non-memory putty-like adhesive or flexible patch disclosed in GB Patent Application No. GB 2 290 974 and European Patent application No. EP 0 686 381 both are secured to the rim of the hole for receiving the stoma.

The ostomy appliances disclosed in GB Patent Application No. GB 2 290 974 and European Patent application No. EP 0 686 381 both suffer from the drawback that the mouldable sealing material is only foreseen to be changed together with the body side member of the appliance. There is no teaching nor indication that the mouldable sealing material might be exchanged separately without removing the body-side member from the skin. Such separate exchange is not possible for either of the embodiments shown in the drawings of these applications.

It has surprisingly been found that it is possible to provide an ostomy appliance having a separate sealing member disposed in the hole of the wafer or pad surrounding the stoma offering a convenient and comfortable solution to the above problems.

None of the above mentioned patents describes the use of a separate sealing member which may be exchanged or substituted separately. Three different types of adhesives can be used for the sealing member, two of which are adaptable to the stoma without the use of tools.

1. Mouldable adhesives which can be adapted to the stoma by displacement, either inwardly or outwardly, of the adhesive mass.
2. Flexible adhesives which can be adapted to the stoma due to the flexibility and compliance whereby they form a protective layer on the peristomal skin surrounding the stoma.
3. Medical grade adhesives known per se but being supplied as a disc having an outer diameter corresponding to the hole in a body side ostomy member and being supplied with a pre-formed hole or for custom-adaptation or fit using a tool and/or a template for use as a sealing member.

This idea according to the invention differs from the above mentioned patents since the central ring in this case can be substituted without substituting the outer adhesive, which carries the bag.

BRIEF SUMMARY OF THE INVENTION

The invention relates in a first aspect to an ostomy appliance comprising a body side member and a sealing member which is removable separately from the body side member when such is in use. More particularly, the body side member has a coupling flange and an adhesive wafer for securing the appliance to the skin, the wafer having a hole for receiving a stoma. The separate sealing member is disposed in the hole of the wafer for surrounding the stoma, and includes an adhesive portion and a backing. The adhesive portion of a hypo-allergenic moldable adhesive is in the form of a moldable mass with an outer diameter that corresponds to the hole in the body side member and an inner diameter defining a hole, the adhesive for adhering to the skin and sealing around the stoma and filling a void between the stoma and the body side member and having sufficient cohesion to be removed in one piece, independently of removal of the body side member when such is in use. The backing covers a surface of the adhesive portion and projects from the outer diameter of the adhesive portion to define a flange which prevents direct contact between exudates and the coupling flange of the body side member.

In a second aspect, the invention relates to an ostomy sealing member having an adhesive portion of hypo-allergenic adhesive in the form of a moldable mass with an outer diameter that corresponds to a hole in a body side ostomy member and an inner diameter defining a hole, the adhesive being adapted to adhere to skin and seal around an ostomy and fill a void between the ostomy and the body side ostomy member and which has a sufficient cohesion to be removed in one piece, independently of removal of the ostomy appliance when such is in use, without leaving remaining residue on the skin or the body side ostomy member. The sealing member also includes a backing which covers a surface of the adhesive and extends out from the outer diameter of the adhesive portion to define a flange which prevents direct contact between exudates and a coupling flange of the body side member during use thereof.

The sealing member may be applied to the abdomen together with the body side member or separately. When applying separately, the sealing member may be placed first and the body side member afterwards or, if desired, vice versa, provided that the outer diameter of the sealing member is smaller than the diameter of the hole in the body side member. Thus, a greater degree of freedom in placing the body side member around the stoma is obtained.

BRIEF DESCRIPTION OF THE DRAWINGS

The invention is disclosed more in detail with reference to the drawings in which.

DETAILED DESCRIPTION OF THE INVENTION

Figure 1:
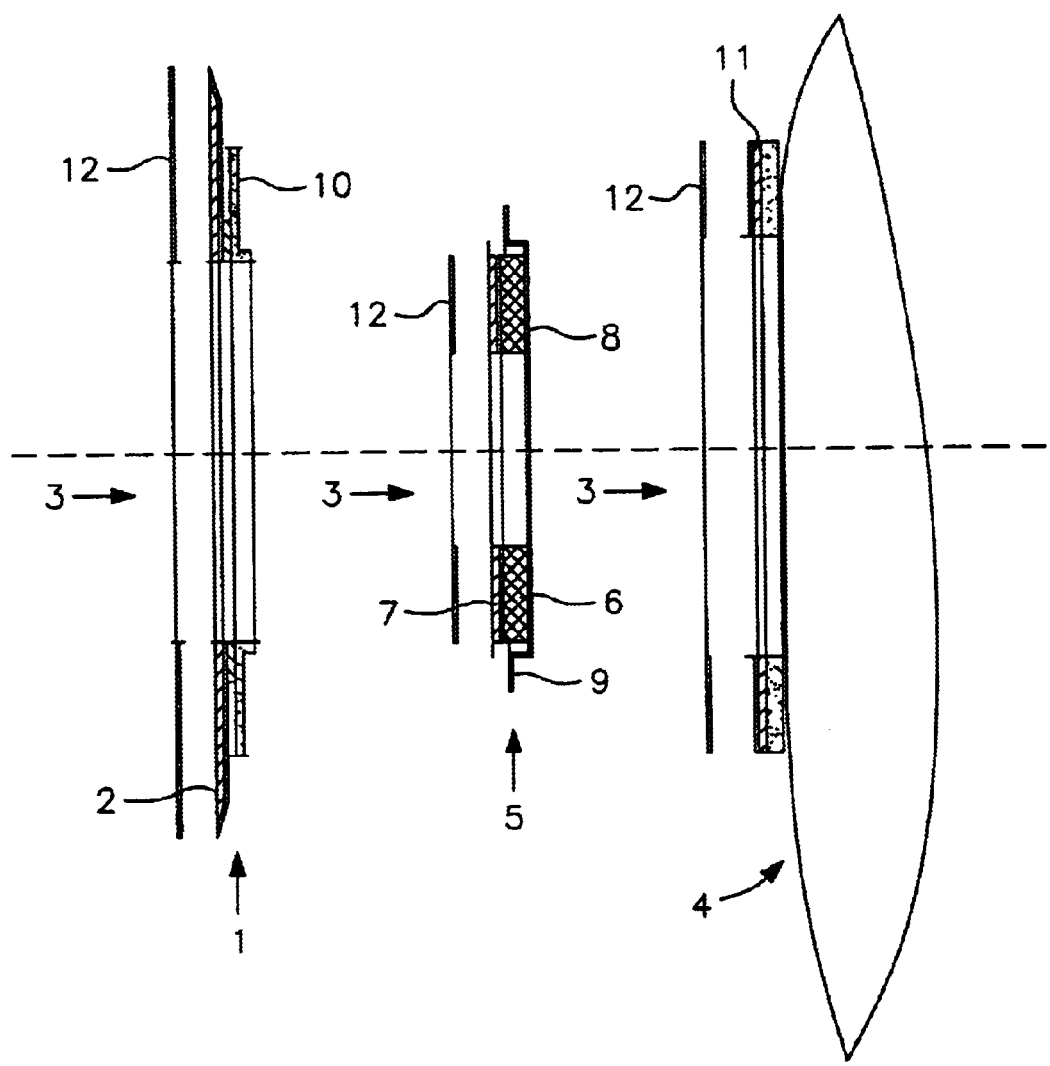
FIG. 1 shows a sectional exploded view of one embodiment of the invention.

Reference is made to FIG. 1 which shows a sectional view of an embodiment of an ostomy appliance of the invention comprising a body side member 1 having an adhesive wafer or pad 2 for securing the appliance to the user's skin (not shown), the wafer or pad having a hole 3 for receiving a stoma, and an optionally separately exchangeable receiving member or bag 4 which may be secured to the body side ostomy member for receiving secretions from the ostomy, the ostomy appliance further comprising a separate sealing member 5 disposed in the hole 3 of the wafer or pad surrounding the stoma. The separate sealing member 5 may be in the form of a ring made from a mouldable adhesive in the form of a paste of a skin-friendly adhesive being sufficiently tacky to secure the appliance or skin barrier to the abdomen and yet having a cohesion ensuring safe removal thereof without leaving residues on the skin. The sealing member 5 may be composed of one material or may optionally be composed of two or more layers 6,7 one of which being a mouldable backing and may optionally be covered with a protecting layer or film 8. In a preferred embodiment of an appliance of the invention, the separate sealing member may further comprise an adhesive layer 9 stretching out from the sealing member for securing the same to the body side member and the receiving member to provide an extra security against leaks and exclude direct contact between the exudates and the coupling flange 10. Thus, pollution or contamination of parts of the body side member during service or exchange of the receiving member or bag is avoided.

In the embodiment of FIG. 1 is shown a ring or flange 10 having a relatively flat surface adapted for receiving an adhesive flange 11 secured to the receiving member for securing the same to the body side member. All adhesive surfaces may be protected by release liners 12 which are removed before application.

The separate sealing member 5 may preferably be a uniform mouldable mass of a hypoallergenic, substantially non-memory putty-like adhesive or it may comprise further constituents such as a protecting film or a mouldable mesh. In other embodiments of the present invention, the sealing member is a uniform mouldable mass of a hypoallergenic mass having a weak elasticity. Such sealing members will allow for an enlargement of the hole for accomodating the stoma when applying the ostomy appliance and will also provide for a snug automatic sealing against the stoma without ligating the same.

The separate sealing member 5 may be substituted together with the receiving member 4 leaving the body side member 1 on the skin. It is contemplated that the sealing member may be substituted independently of the receiving member according to the need of the user.

Figure 2:
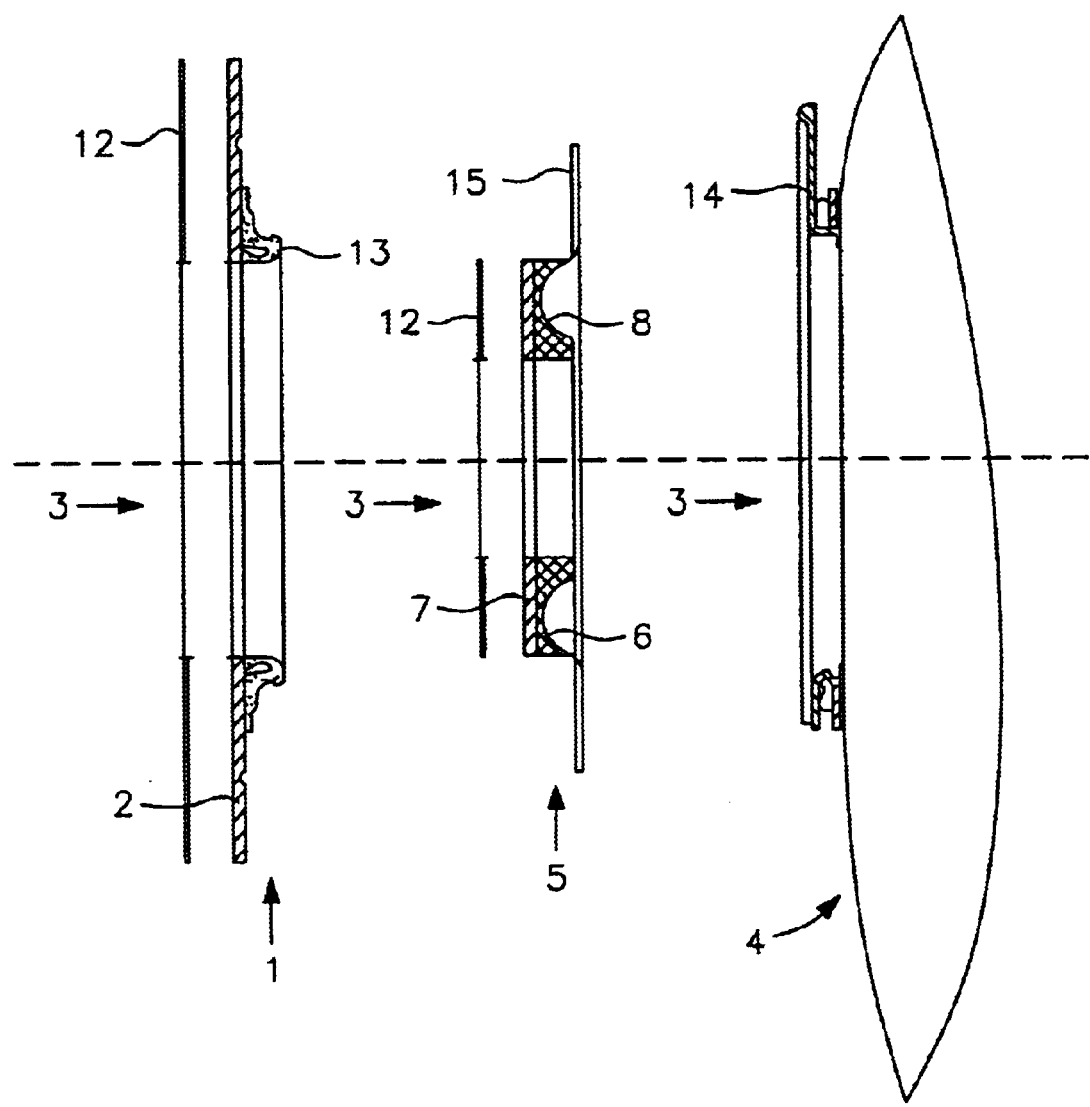
FIG. 2 shows a sectional exploded view of another embodiment of the invention.

Now referring to FIG. 2, there is described another embodiment of an ostomy appliance of the invention comprising a body side member 1 having an adhesive wafer or pad 2 for securing the appliance to the user's skin (not shown), the wafer or pad having a hole 3 for receiving a stoma, and an optionally separately exchangeable receiving member or bag 4 secured to the body side ostomy member for receiving secretions from the ostomy, the ostomy appliance further comprising a separate sealing member 5 disposed in the hole 3 of the wafer or pad surrounding the stoma. The separate sealing member 5 may be in the form of a ring made from a paste of a skin-friendly adhesive being sufficiently tacky to secure the appliance or skin barrier to the abdomen and yet having a cohesion ensuring safe removal thereof in one piece, independently of removal of the body side ostomy when such is in use, without leaving adhesive residues on the skin or body side ostomy member. The sealing member may be composed of one material or may optionally be composed of two or more layers 6,7, one of which being a mouldable backing and may optionally be covered with a protecting film or backing B. In one embodiment of an appliance of the invention, the separate sealing member may further comprise a flange 15 stretching out beyond the layers 6, 7 for providing an extra security against leaks and to exclude direct contact between the exudates and the coupling ring 13. Thus, pollution or contamination of parts of the body side member during service or exchange of the receiving member or bag is avoided.

In the embodiment of FIG. 2 is shown a coupling ring 13 adapted for receiving a coupling to a corresponding mechanical coupling member 14 known per se which is secured to the receiving member for securing the same to the body side member and for providing security against leaks. All adhesive surfaces may be protected by release liners 12 which are removed before application.

The separate sealing member 5 may preferably be a uniform mouldable mass of a hypoallergenic, substantially non-memory putty-like adhesive or it may comprise further constituents such as a protecting film or a mouldable mesh.

The separate sealing member 5 may be replaced together with the receiving member 4 leaving the body side member 1 on the skin.

In the different embodiments of compositions of the sealing member shown in FIGS. 3–10, all adhesive surfaces may be protected by release liners which are removed before application.

Figure 3:
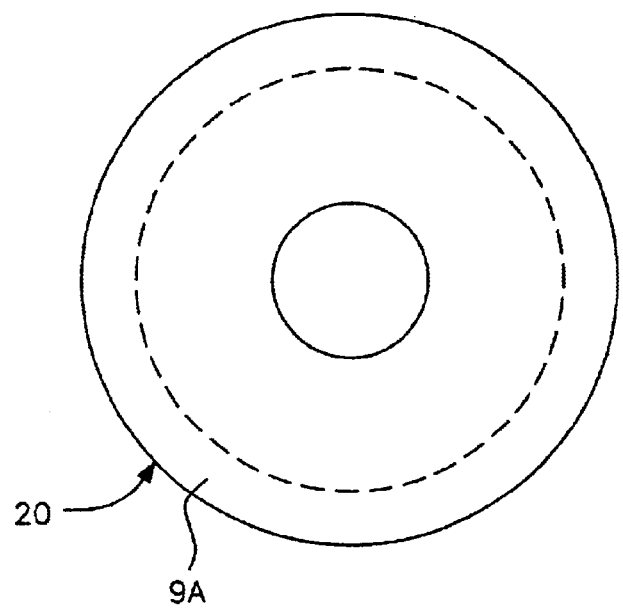
FIG. 3 shows a top view of an embodiment of an ostomy sealing member according to the invention in the form of a mouldable adhesive ring.
Figure 4:
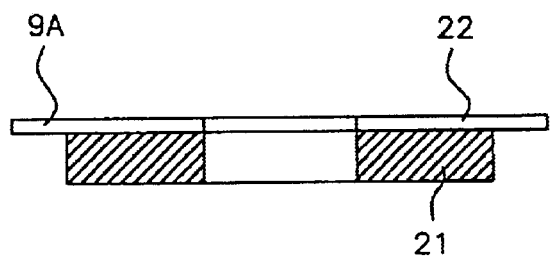
FIG. 4 shows a cross sectional view of the embodiment of FIG. 3.

Reference is made to FIGS. 3 and 4. A sealing member in the form of a mouldable adhesive ring 20 has a centrally located opening. The mouldable adhesive ring is applied by placing the opening over the stoma and adjusting it to the stoma by displacing the adhesive mass inwardly by finger pressure whereby it forms a protective mass surrounding the stoma. The mouldable adhesive may also be adjusted to the stoma by displacing the adhesive radially outwardly to adapt the hole to the size and the shape of the stoma before application.

The mouldable ring may be a composite made of two different materials laminated together: a mouldable adhesive layer 21 and a mouldable backing 22. The mouldable adhesive may be composed of a hypo-allergenic, soft, easily-deformable, non-memory putty-like adhesive material having an outer diameter that corresponds to a hole in a body side ostomy member and an inner diameter defining a hole. The adhesive is adapted to adhere to the skin and seal around an ostomy, filling a void between the ostomy and the body side ostomy member, and is preferably a hydrocolloid-based adhesive or a hydrogel. The mouldable backing may, e.g., be a PARAFILM or made from a polymer solution which is sprayed on the surface and protects the surface of the adhesive against dissolution by secretions from the stoma and prevents a tacky surface on the side facing the bag. The mouldable backing covers a surface of the adhesive material and stretches out beyond the outer diameter of the putty-like adhesive material to define a flange 9A which may be adhesive.

This embodiment offers the following advantages: it is simple/easy to handle, it may be adapted to a stoma without use of tools, and it may easily be adapted to complicated shapes of the stoma.

Figure 5:
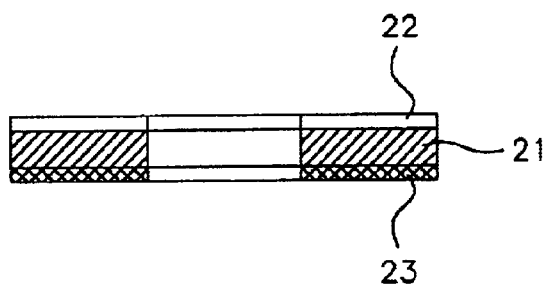
FIG. 5 shows an alternative cross sectional view of an ostomy sealing member of the embodiment of FIG. 3.

In the embodiment shown in the form of a sectional view in FIG. 5, the mouldable ring is made in the form of a composite made of three different materials laminated together: a medical grade adhesive 23, a mouldable adhesive mass 21, and a mouldable backing 22.

The medical grade adhesive secures the sealing member to the peristomal skin. A variety of such barrier adhesives are known in the art and may be used here, one such formulation being disclosed, for example in DK patent DK 147035 and U.S. Pat. No. 4,551,490. The mouldable adhesive mass is laminated on top of the medical grade adhesive and is used for adapting the sealing member to the stoma by displacing the material. The mouldable adhesive may be composed of a hypoallergenic, soft, easy-deformable, non-memory putty like adhesive material and is preferably a hydrocolloid based adhesive or a hydrogel. The mouldable backing, e.g. Para-Film® or a polymer solution which is sprayed on the surface, protects the surface of the mouldable mass against dissolution by secretions from the stoma and prevents a tacky surface on the side facing the bag.

The medical grade adhesive improves the performance due to elimination of the risk of dissolution of the mouldable adhesive mass. It also eliminates the risk of having residues from the mouldable material remain on the skin after removal. The best performance is achieved if the medical grade adhesive is extended to cover the edges of the mouldable adhesive in order to protect the edges from erosion and dissolution.

This embodiment offers the following advantages: it is simple/easy to handle, it may be adaptated to stoma without use of tools, it gives rise to no or very little residue on skin after removal, it gives rise to no or little erosion of adhesive, and it may easily be adaptated to complicated shapes of the stoma.

Figure 6:
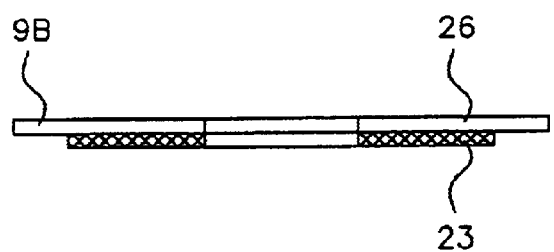
FIG. 6 shows another alternative cross sectional view of a further embodiment of an ostomy sealing member of the embodiment.

In the embodiment shown in the form of a sectional view in FIG. 6, a flexible ring is made in the form of a composite made of two different materials laminated together: a medical grade adhesive 23, and a flexible backing 26. The flexible backing 26 stretches out beyond the outer periphery of the adhesive 23 in the form of a flange 9B.

The medical grade adhesive secures the unit to the peristomal skin. The flexible backing, protects the surface of the adhesive against dissolution by secretions from the stoma and prevents a tacky surface on the side facing the bag.

The ring may be reinforced at the edge in order to ease the handling of the ring at application. This can be done by lamination of a ring body to the edge of the adhesive ring. The ring body may be made of a foam material or any other material having sufficient strength to reinforce the edge without hindering the flexibility.

This embodiment offers the following advantages: it is simple/easy to handle, it may be adapted to the stoma without the use of tools, it gives rise to no or very little residue on the skin after removal, and it gives rise to no or little erosion of adhesive.

Figure 7:
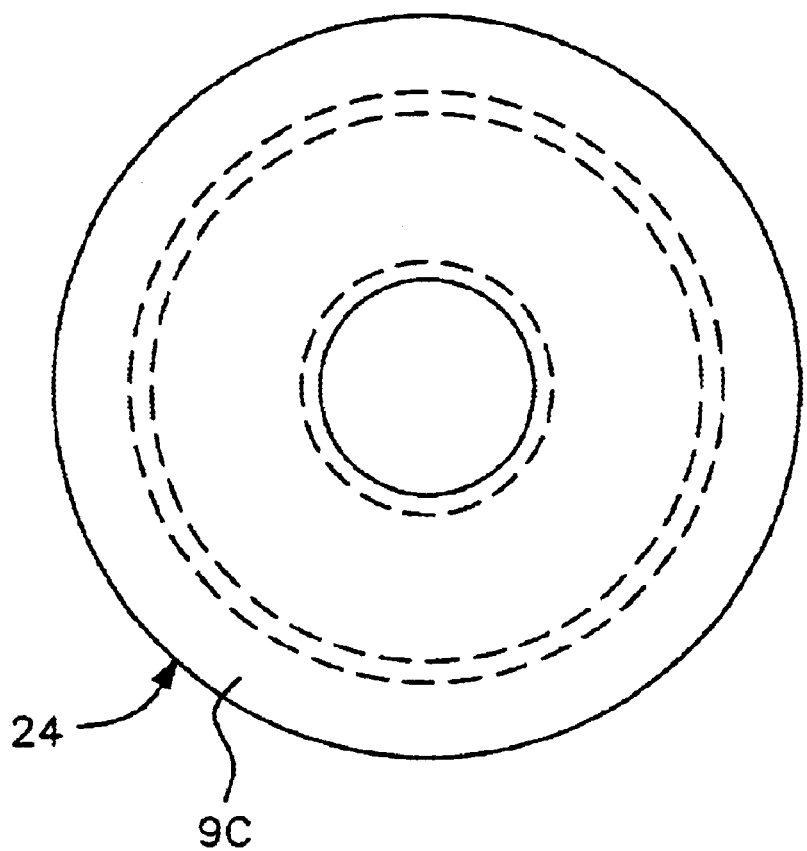
FIG. 7 shows a top view of yet another embodiment of an ostomy sealing member according to the invention in the form of a wrapped up mouldable adhesive ring.
Figure 8:
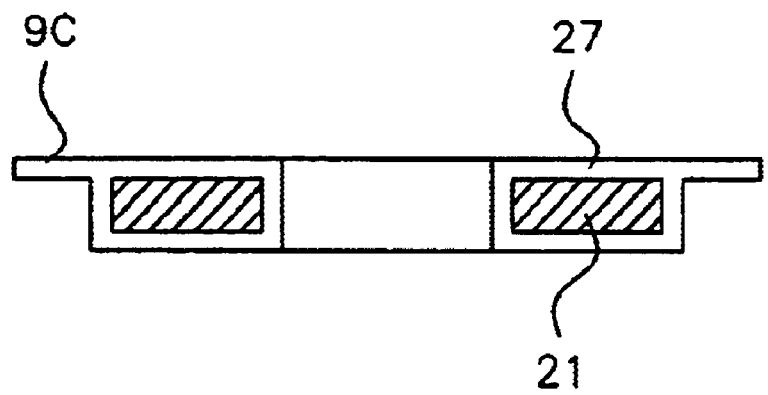
FIG. 8 shows a cross sectional view of the embodiment of FIG. 7.

Reference is made to FIGS. 7 and 8. The mouldable ring 24 is made as composite material made of two different materials, a wrapping material 27 and a core material 21. The wrapping material stretches out beyond the periphery of the core 21 in the form of a flange 9C which may be adhesive.

The core material is a soft, easy deformable, non-memory putty like material. The core material is used for adapting the unit to the stoma by displacing the material inwardly to the stoma by finger pressure.

The wrapping material is thin, flexible and deformable. The wrapping material may be a water permeable membrane coated with a skin-friendly adhesive on the outer side, e.g., product 1527 from 3M. The wrapping material may also be a skin-friendly hydrocolloid-containing barrier adhesive. A variety of such barrier adhesives are known in the art and may be used here, one such formulation being disclosed, for example, in DK patent 147035 and U.S. Pat. No. 4,551,490. The wrapping material improves the performance of the mouldable ring due to elimination of the risk of dissolution of the deformable core material. This also eliminates the risk of residues from the core material remaining on the skin after removal.

This embodiment offers the following advantages: it is simple/easy to handle, it may be adapted to stoma without use of tools, it gives rise to no or very little residue on skin after removal, it gives rise to no or little erosion of adhesive, and it may easily be adapted to complicated shapes of the stoma.

Figure 9:
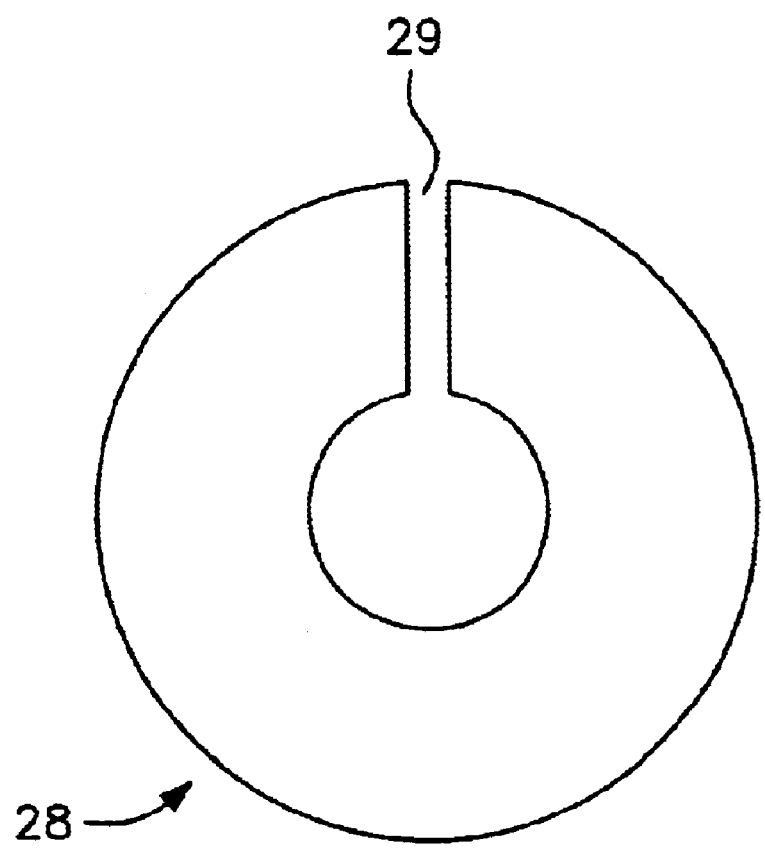
FIG. 9 shows a top view of a further embodiment of an ostomy sealing member according to the invention in the form of an open flexible adhesive ring.
Figure 10:
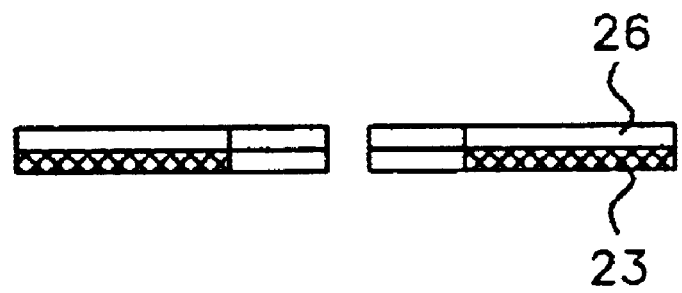
FIG. 10 shows a cross sectional view of the embodiment of FIG. 9.
Figure 11:
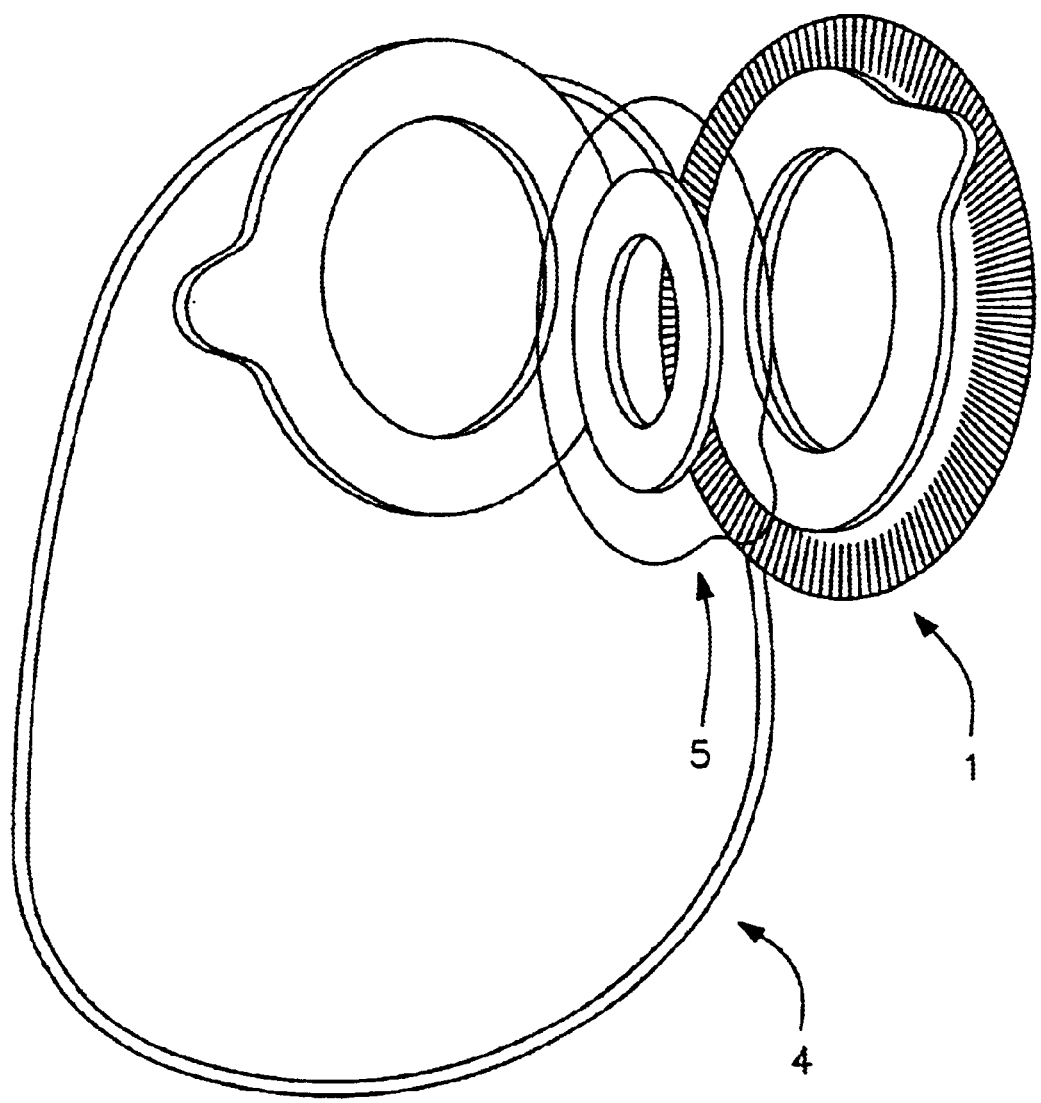
FIG. 11 shows the parts of an ostomy appliance according to the invention.

Reference is made to FIGS. 9 and 10. The sealing member is in the form of an open flexible ring 28 having a centrally located opening and a slot 29. The open ring is made as a composite material made of 2 different materials, a medical grade adhesive 23 and a flexible backing 26.

The flexible adhesive ring is applied by placing the ring around the stoma and adjusting the adhesive to the stoma by pulling the ends of the open ring together. The adhesiveness of the ring will keep it in the form of a ring when formed.

The medical grade adhesive secures the unit to the peristomal skin. The flexible backing protects the surface of the adhesive against dissolution by secretions from the stoma and prevents a tacky surface on the side facing the bag.

The ring may be reinforced at the edge in order to ease the handling of the ring on application. This can be done by lamination of a ring body to the edge of the adhesive ring. The ring body may be made of a foam material or any other material having sufficient strength to reinforce the edge without hindering the flexibility.

This embodiment offers the following advantages: it is simple/easy to handle, it may be adapted to stoma without use of tools, it gives rise to no or very little residues on skin after removal, and it gives rise to no or little erosion of adhesive.

Figure 12:
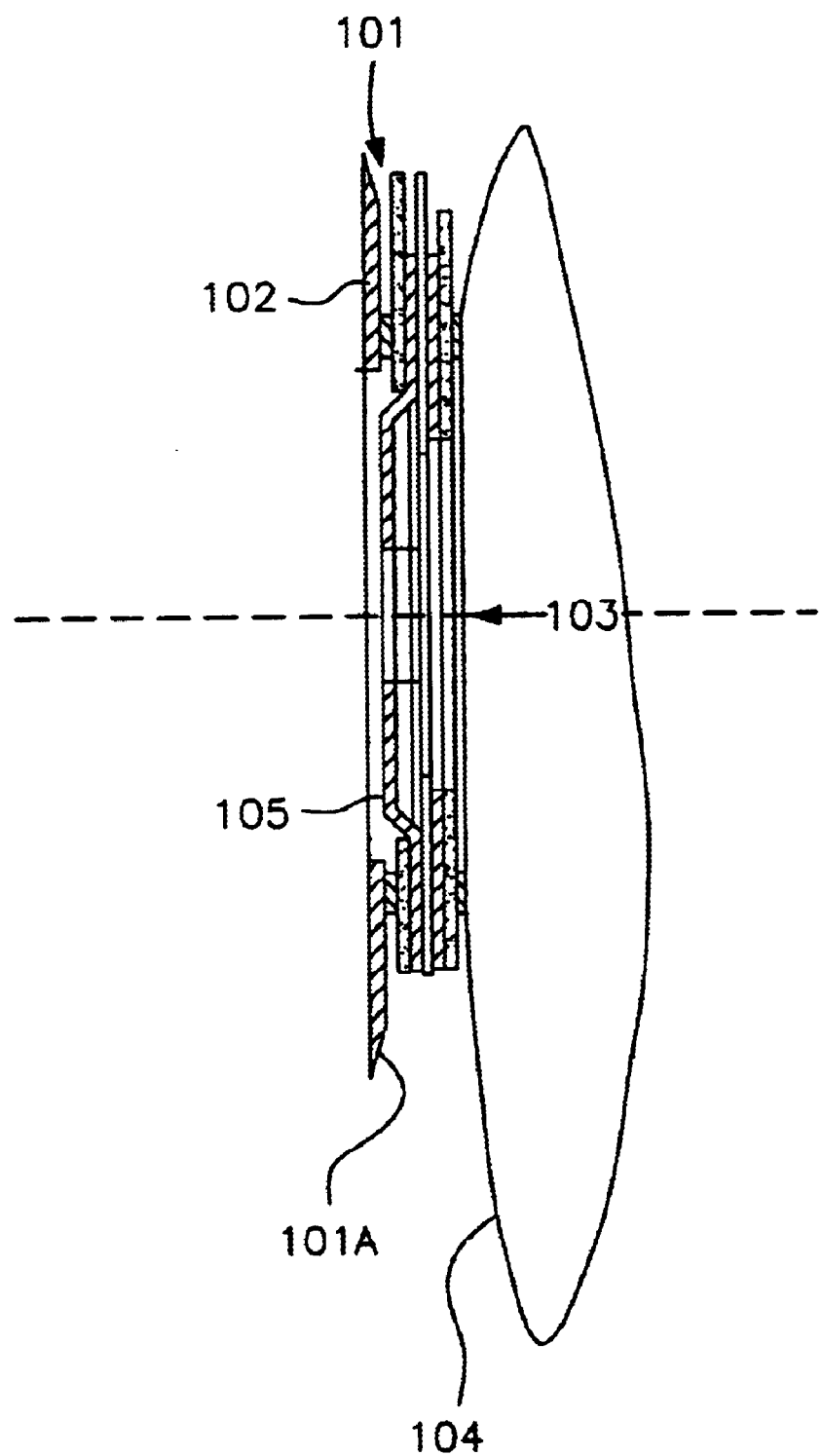
FIG. 12 shows a cross sectional view of a third embodiment of an ostomy appliance according to the invention.

Reference is made to FIG. 12 which shows an ostomy appliance according to the invention comprising a body side member 101 having an adhesive wafer or pad 102 for securing the appliance to the user's skin, the wafer or pad having a hole 103 for receiving a stoma, and a separately exchangeable receiving member or bag 104 which may be secured to the body side ostomy member for receiving secretions from the ostomy, the ostomy appliance further comprising a separate sealing member 105 disposed in the hole of the wafer or pad surrounding the stoma. The edges 101A of the ostomy body side member are preferably bevelled.

Figure 13:
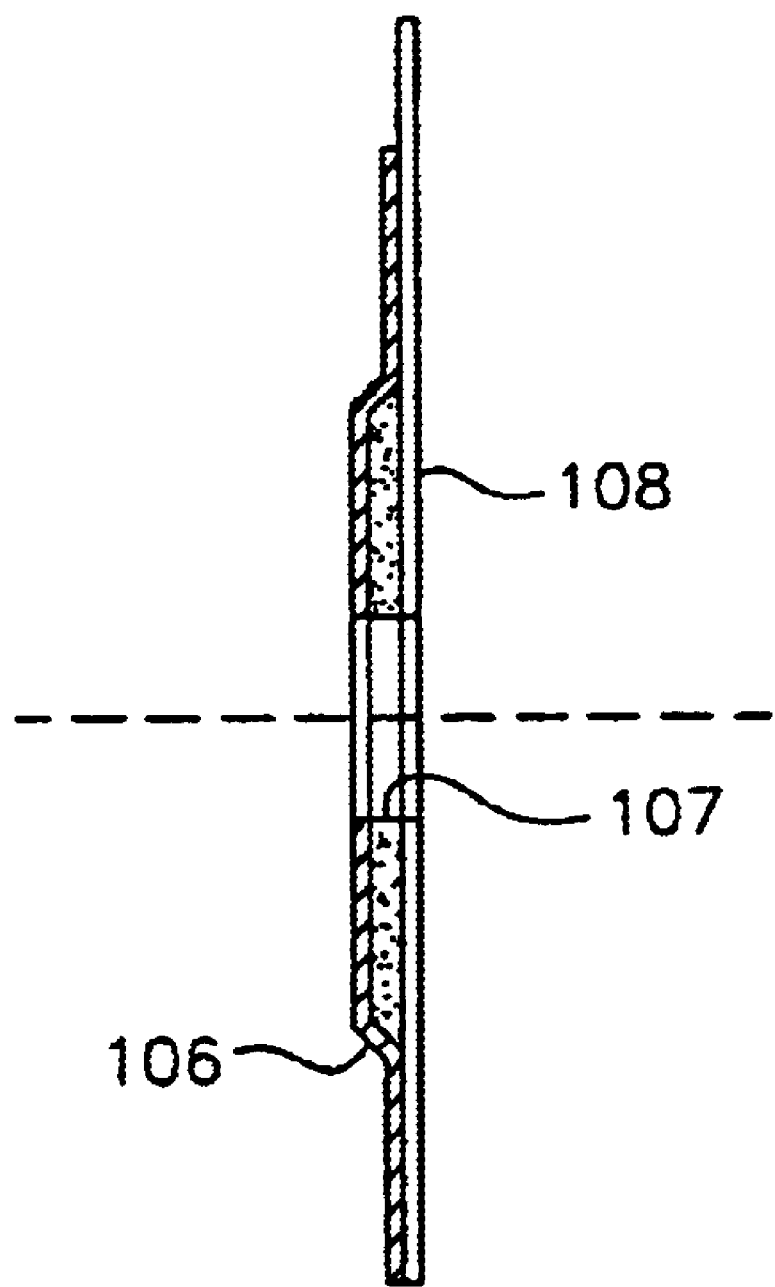
FIG. 13 shows a cross sectional view of another embodiment of a sealing member according to the invention.

Reference is made to FIG. 13. In this embodiment a layer 106 of a skin friendly adhesive, preferably a medical grade adhesive is positioned on the proximal side of the mouldable adhesive mass 107 of the separate sealing member. Such a layer is preferred if the mouldable adhesive mass 107 of the separate sealing member does not have a sufficient cohesion to be removed without leaving residues on the skin. Furthermore, the separate sealing member comprises a mouldable backing 108. The sealing member may be open in that the mouldable adhesive mass 107 may be squeezed out between the layer 106 and the mouldable backing 108 in order to seal against the ostomy. In the alternative, the mouldable adhesive mass may be fully enclosed in a thin, flexible and deformable material (wrapping material) allowing for deformation of the mouldable adhesive mass and a sealing against the ostomy. In a preferred embodiment the sealing member has a flange stretching from the outer rim thereof. The adhesive 106 is preferably an adhesive which may be sterilized using ethylene oxide.

Figure 14:
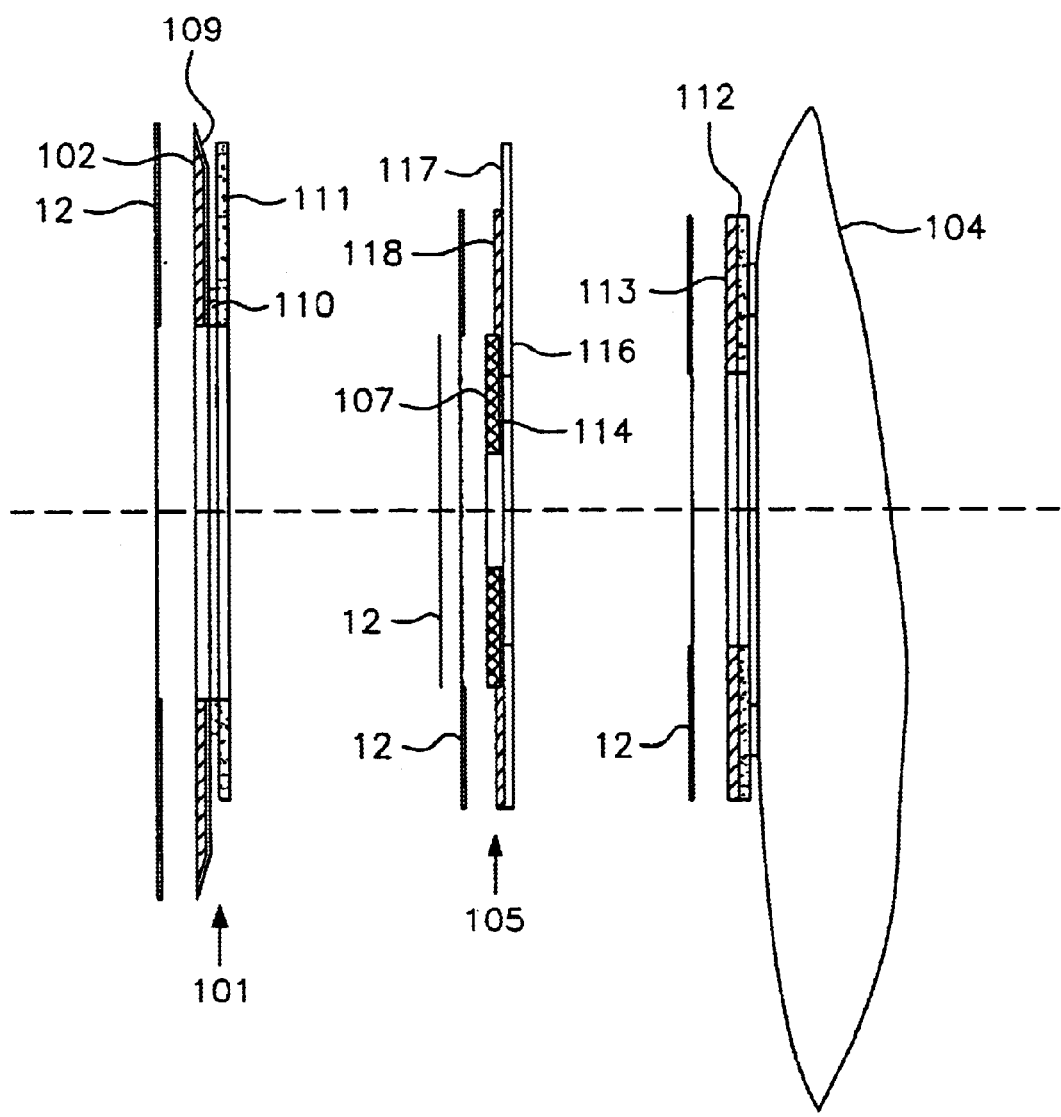
FIG. 14 shows a sectional exploded view of a fourth embodiment of an ostomy appliance of the invention.

In the preferred embodiment of FIG. 14, the body side member 101 comprising an adhesive wafer or pad 102 for securing the appliance to the user's skin, the adhesive being covered by a film 109 conventionally used. Furthermore, the body side member is secured by a sealing 110 to a flange 111, preferably made from a foam material. The receiving member or bag 104 comprises a flange 112 secured to the flange 111 by a layer of an adhesive 113. The flange 111 preferably stretches beyond the inner rim of the wafer or pad 102 in order to prevent that the mouldable adhesive mass 107 of the separate sealing member adhering to the wafer or pad. Such adherence might prevent the separate exchange of the sealing member independently of the exchange of the body side member. The separate sealing member may comprise a sheet 116 for adhering to the flange of the body side member and for adhering the exchangeable receiving member or bag. At the outer rim of the flange 111, the sheet 116 preferably stretches beyond the rim of the flange to provide a handle 117 for gripping for separate exchange of the sealing member. An adhesive 118 is present on the face of the sheet 116 for securing the sheet to the flange 111. The adhesive 113 may be any adhesive being detachable from the two flanges in order to allow for an exchange of only the receiving member or bag leaving the body side member and the separate sealing member on the abdomen of the ostomate. It is desirable that the attachment between the receiving member or bag and the separate sealing member is weaker than the attachment between the separate sealing member and the body side member. The adhesive 113 may be an acrylic adhesive or any conventional skin friendly adhesive. Furthermore, the separate sealing member comprises a mouldable backing 114. The backing preferably has a tensile strength of 2–5 N/M$^2$ at elongations up to 300%.

The separate sealing member 105 may be made from a mouldable adhesive in the form of a paste of a skin-friendly adhesive being sufficiently tacky to secure the appliance or skin barrier to the abdomen and yet having a cohesion ensuring safe removal thereof without leaving residues on the skin. The sealing member may be composed of one material or may optionally be composed of two or more layers, one of which being a mouldable backing, and may optionally be covered with a protecting layer or film.

All adhesive surfaces may be protected by release liners 12 which are removed before application.

The separate sealing member 105 may preferably be a uniform mouldable mass of a hypoallergenic, substantially non-memory putty-like adhesive or it may comprise further constituents such as a protecting film or a mouldable mesh.

The separate sealing member 105 may be substituted together with the receiving member 104 leaving the body side member 101 on the skin. It is contemplated that the sealing member may be substituted independently of the receiving member according to the need of the user.

Figure 15:
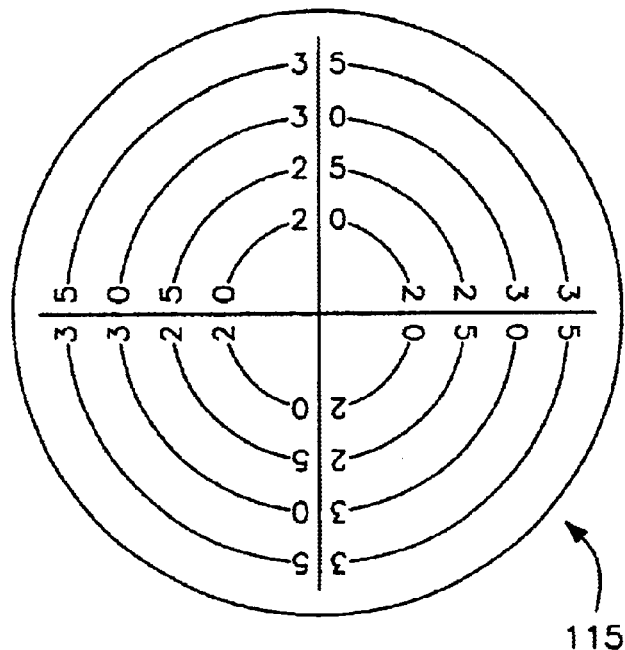
FIG. 15 shows a release liner having an indication of the size of the hole of an ostomy appliance of the invention for accommodating an ostomy.

Now referring to FIG. 15, there is shown a release liner 115 having an indication of the size of the hole of an ostomy appliance of the invention for accommodating an ostomy, at the side in contact with the separate sealing member (distal as compared to the ostomy). In the alternative, the indication may be placed on the side facing away from the separate sealing member (proximal as compared to the ostomy) if the release liner is transparent.

Figure 16:
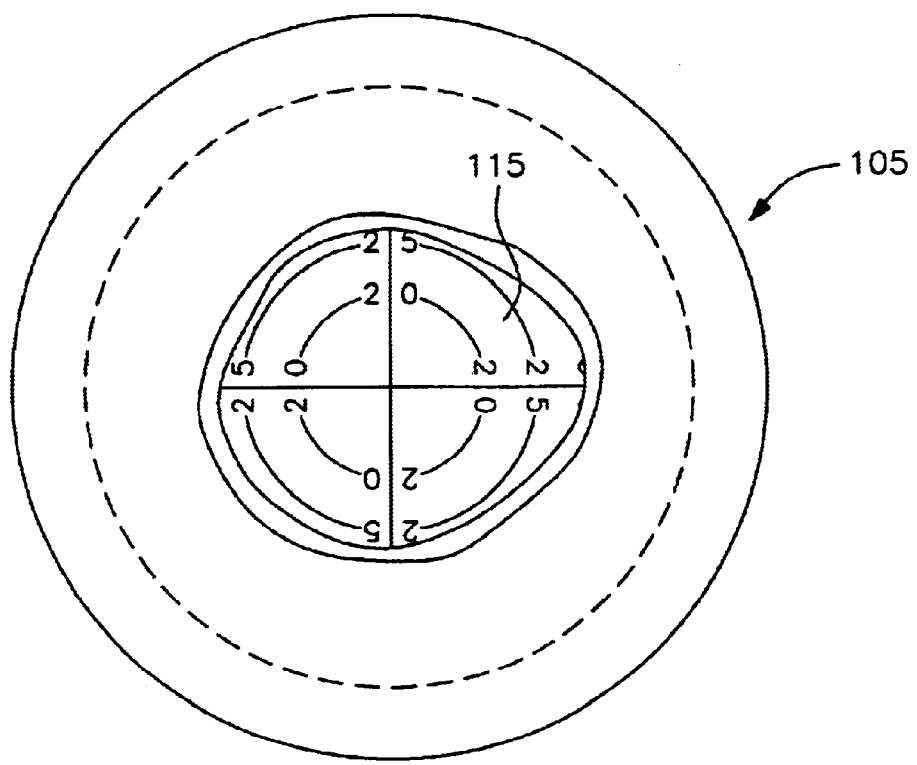
FIG. 16 shows a view from the distal side of the separate sealing member of an ostomy appliance of the invention in which the separate sealing member has been partially everted to increase the size of the hole of an ostomy appliance of the invention for accommodating an ostomy and showing the indication of the size of the hole placed on the release liner below.

FIG. 16 shows a view from the distal side of the separate sealing member 105 of an ostomy appliance of the invention in which the separate sealing member has been partially everted to increase the size of the hole of an ostomy appliance of the invention for accommodating an ostomy and showing the indication of the size of the hole placed on the release liner 115 below.

Figure 17:
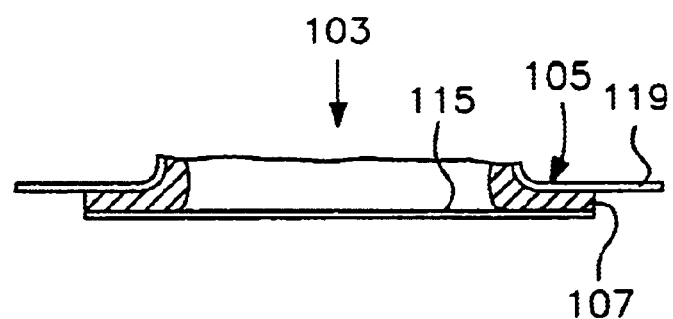
FIG. 17 shows a cross sectional view of the separate sealing member of FIG. 16.

FIG. 17 shows a cross sectional view of the separate sealing member of FIG. 16 wherein the sealing member 105 in the form of a uniform mouldable mass 107 has been partially everted to enlarge the hole 103 and reveal a larger part of the surface of the release liner 115 below and of the indication of the size of the hole.

The mouldable adhesive and the adhesive wafer may be composed of a hypoallergenic, soft, easily-deformable adhesive material and is preferably a hydrocolloid-based adhesive or a hydrogel. The mouldable backing 119 may, e.g., be PARAFILM or made from a polymer solution which is sprayed on the surface and protects the surface of the adhesive against dissolution by secretions from the stoma and prevents a tacky surface on the side facing the bag. The mouldable backing 119 stretches out beyond the outer periphery of the mass 107 in the form of a flange or adhesive layer.

Figure 18:
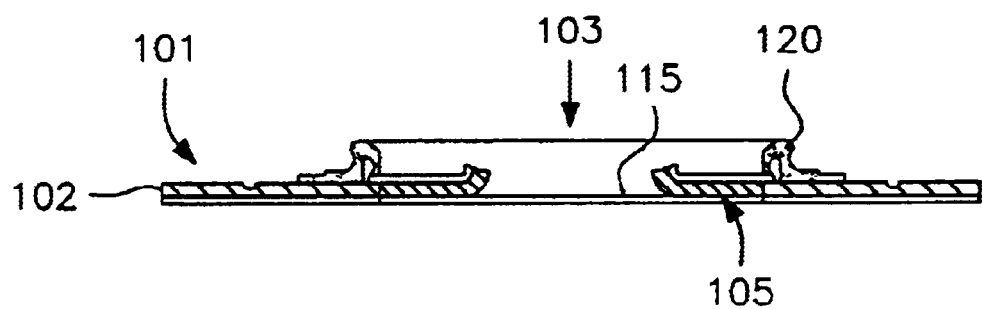
FIG. 18 shows a cross sectional view of an embodiment of an ostomy appliance body side member according to the invention.

FIG. 18 shows a cross sectional view of an embodiment of an ostomy appliance body side member 101 according to the invention comprising an adhesive wafer or pad 102 for securing the appliance to the user's skin; the adhesive may be covered by a film as is conventionally used. Furthermore, the body side member comprises a separate sealing member 105 disposed in the hole of the wafer or pad surrounding the stoma and a release liner 115. A receiving member or bag may be secured to a coupling ring 120.

The present invention relates to an ostomy appliance comprising a body side member comprising an adhesive wafer or pad for securing the appliance to the user's skin, the wafer or pad having a hole for receiving a stoma, and an optionally separately exchangeable receiving member or bag secured to the body side ostomy member for receiving secretions from the ostomy the ostomy appliance further comprising a separate sealing member disposed in the hole of the wafer or pad surrounding the stoma.

The mouldable adhesive used in the different compositions of the sealing member is preferably characterised as being a hypoallergenic, substantially non memory putty-like adhesive. It may, e.g. be a homogeneous mixture of a pressure sensitive adhesive component, mineral oil, and hydrocolloid gums or cohesive strengthening agents as the mass disclosed in U.S. Pat. No. 4,204,540. The mass may also be a composition including one or more hydrocolloids, a film former which is butyl ester of polycarboxylic resin formed from vinyl methyl ether and maleic anhydride, a plasticizer, a thickening agent and an alcohol solvent as disclosed in EP Patent No. 0 048 556. A further paste is disclosed in U.S. Pat. No. 5,369,130. This composition comprises a liquid rubber component and a filler component. The rubber component is a diene-type liquid rubber, preferably butadiene- or isoprene-type. The filler component is selected from the groups consisting of inorganic fillers, natural polymers, semi-synthetic water-soluble polymers and synthetic water-soluble polymers. A further composition of a skin protective gel containing polyvinyl methylether or monoisopropyl ester of polyvinylmethylether maleic acid is disclosed in U.S. Pat. No. 3,876,771. The composition is a made up of a film-forming protective colloidal material in combination with a solvent and a gelling agent. Isopropanol is the solvent, monoisopropyl ester of polyvinyl methylether/maleic acid is a film former and polyvinylpyrrolidone, polyvinyl methylether, polyacrylic acid and hydroxypropyl cellulose are the gelling agents. A hydrophilic elastomeric pressure sensitive material is disclosed in U.S. Pat. No. 4,750,482. This composition is a water-insoluble, hydrophilic, pressure-sensitive adhesive including at least one irradiation cross-linked synthetic organic polymer (predominantly of derived from vinylpyrrolidone) and an adhesive plasticizer (polyethylene glycol).

The composition disclosed in EP 0 048 556 B1 suffers from the drawback that it comprises a considerable amount (25% to 45% by weight) of alcohol, ethanol and isopropanol being preferred. When using such a paste, there is only a limited time for forming the paste after the application as the paste cures when exposed to air. Furthermore, the amount of alcohol trapped in the paste must be minimized in order to avoid less attractive physical properties due to an adverse effect on the properties of the adhesive of an ostomy appliance which is placed on the paste. Still further, the considerable amount of alcohol may irritate the skin and such a composition is not advisable to use on skin which has been sensitized.

The pastes disclosed in U.S. Pat. No. 4,204,540 suffer from the drawback that the shapeability is very dependant on the content of the mineral oil. If an insufficient amount of mineral oil is added to the composition, it will be too tough to shape and if too much mineral oil is added to the composition it becomes sticky and difficult to handle. Generally, pastes consisting of polyisobutylene, butyl rubber and mineral oil may be very hard, if the content of butyl rubber is high and hence the paste will be difficult to shape, or it will be very soft and liquid if the content of butyl rubber is low and the content of mineral oil is high.

The mass used according to the invention is preferably in the form of a mouldable mass of a hypo-allergenic, substantially non-memory putty-like adhesive. In accordance with a preferred embodiment of the invention, the sealing member is made from a mouldable mass of a hypoallergenic, substantially non-memory putty-like adhesive comprising a) a block copolymer having a major content of di-block copolymer, b) a tackifying liquid constituent, and c) a waxy constituent.

The content of block copolymer is preferably from 1 to 20% by weight, the content of tackifying liquid is preferably from 5 to 60% by weight, and the content of waxy constituent is preferably from 1 to 10% by weight, calculated on the total composition of the mass.

The mouldable mass further comprises one or more optional constituents such as petroleum jelly in an amount of up to 20% by weight, polybutylene oil in an amount of up to 30% by weight and/or liquid paraffin in an amount of up to 30% by weight.

The block copolymer preferably has a low molecular weight and a high content of di-block component. The molecular weight of the block copolymer is from 20,000 to 150,000, preferably from 30,000 to 100,000. The content of diblock copolymer in the block coplolymer is preferably above 10%, more preferred above 25% and more preferred above 30%. The content of diblock copolymer imparts cohesion to the mass and renders the mouldable mass less elastic than a corresponding mass comprising a threeblock copolymer due to a minor degree of physical cross-linking and imparts to the plasticity or substantially non-memory putty-like characteristics of the mass.

The mouldable masses of the invention comprise a tackifying viscous liquid constituent. The action of the tackifying liquid constituent is to plasticize and tackify the copolymer. Such a plasticizer should be compatible with the copolymer as compatibility with the copolymer ensures that the adhesive may be removed as an integrated unit.

Furthermore, the mouldable masses of the invention comprise a waxy constituent. The role of the waxy constituent is to render the mass plastic and mouldable and impart non-memory characteristics to the mass.

The block copolymer may be a copolymer comprising a block of a relatively hard polymer which may form physical cross-linking and a block of a softer polymer. The constituents of the block copolymer may be the same as are conventionally used for block copolymers such as SBS, SIS or SEBS copolymers, e.g., styrene and butadiene, isoprene or ethylenebutylene copolymers. The preferred copolymer is a SEBS (styrene-ethylenebutylene-styrene copolymer) having a content of diblock component above 30%.

The tackifying viscous liquid constituent is preferably a viscous polymeric material compatible with the block copolymer. The tackifying liquid may be a polybutylene or polyisobutylene and is preferably a saturated component which cannot give rise to chemical cross-linking deteriorating the non-memory putty-like characteristics of the mass. The tackifying liquid component is preferably a polybutylene and more preferably polyisobutylene. The molecular weight of a tackifying viscous polymeric component is preferably from 10,000 to 120,000 when determined by GPC.

The mouldable mass may, if required, comprise a further oily plasticizer for plasticizing the SEES and polyisobutylene/polybutylene in order to reduce the elasticity. Such an oily plasticizer is suitably a viscous polymeric material having molecular weight from 300 to 10,000 when determined by GPC.

The mouldable mass may comprise a tackifier increasing the adhesive properties of the composition in order to ensure a good contact between the appliance and the skin. Such a tackifier is preferably a hydrocarbon tackifier homogeneously distributed in the mass. The tackifier is preferably a terpene tackifier resin or a dicyclopentadiene tackifier resin. Especially preferred according to the invention as hydrocarbon tackifier resins are polymers and copolymers of dicyclopentadiene, alpha-pinene and/or beta-pinene.

The waxy component may, e.g., be a mineral wax or petroleum jelly and is most preferably a microcrystalline wax which is compatible with the preferred blockcopolymer SEBS.

In accordance with a preferred embodiment of the invention, the mass comprises a hydrocolloid which is able to absorb moisture or liquids from the body and thus to increase the wearing-time of the adhesive and thus of the ostomy appliance. A hydrocolloid component may, e.g., be a water absorbing and water swellable component mixable with the main components of the mass. Any hydrocolloid known per se for ostomy or wound care purposes may be used. The hydrocolloid may, e.g., be sodium carboxymethylcellulose (CMC), hydroxyethylcellulose, pectin, gelatine, guar gum, karaya, locust bean gum, carrageenan, xanthan, or sodium or calcium alginate. A hydrocolloid will typically be present in an amount of from 20 to 70% by weight of the total composition in order to have a sufficient absorbent capacity and still retain the characteristics of the mouldable mass. More preferably, the total amount of hydrocolloids is from 30 to 60%, and most preferably the total amount of hydrocolloids is from 45 to 60% by weight.

For some purposes it is suitable also to include smaller amounts of a filler in the mass of the invention which may add to the cohesion and also contribute to the plasticity. Such filler may, e.g., be any filler known per se for ostomy or wound care purposes such as talc, calcium carbonate, china clay, zinc oxide or the like. Such filler may constitute up to 3–20% by weight of the composition.

Still further, the masses used according to the invention may optionally comprise further constituents such as emollients, disinfecting agents and/or bactericidal agents known per se for use for ostomy or wound care purposes.

An especially preferred embodiment of the invention is constituted by a mouldable mass comprising SEBS, polybutene, polybutene oil, a tackifier resin, microcrystaline wax, CMC, pectin, gelatine and zinc white.

The sealing member may according to the invention be in the form of a paste or in the form of a mouldable ring comprising a hypoallergenic, substantially non-memory putty-like adhesive. In one embodiment of the invention, the sealing member is in the form of a mouldable ring having a slot for facilitating adaptation to stomas having a small diameter.

In another embodiment of the invention, the mouldable mass used is a pressure sensitive adhesive composition suitable for application to human or animal skin comprising a water dispersible polymer.

Such a pressure sensitive adhesive composition may, in a preferred embodiment, comprise a water dispersible polymer, one or more polymer(s) selected from the group consisting of polyolefins or copolymers or blends thereof, one or more physically cross-linked elastomers selected from block copolymers comprising styrene and one or more olefins, polyethylene glycols and glycerol; optionally a butene polymer or copolymer, optionally a tackifying resin which may be partly or totally hydrogenated, optionally a microcrystalline wax, optionally a plasticizer, optionally one or more hydrocolloids and optionally a pigment.

By introducing a water dispersible polymer in a self-adhesive elastomeric matrix an improved adhesion in moist environment is achieved. This is ascribed to the fact that the water dispersible polymer is present at the surface of the adhesive agent and thus is able to cause an immediate absorption of water. The water-absorbing polymer furthermore remains sticky after having absorbed water which is in contrast to the non-absorbing elastomers used in conventional skin friendly adhesives and hence, a better adhesion over longer periods of time is obtained.

Such a pressure sensitive composition typically comprises 10–50% of a water dispersible polymer, 10–70% of one or more polymer(s) selected from the group consisting of polyolefins or copolymers or blends thereof, one or more physically cross-linked elastomers selected from block-copolymers comprising styrene and one or more olefins, polyethylene glycols and glycerol; 0–15% of a butene polymer or copolymer, 0–30% of a tackifying resin which may be partly or totally hydrogenated, 0–10% of a microcrystalline wax, 0–10% of a plasticizer, 0–50% of one or more hydrocolloids and 0–5% of a pigment.

The water dispersible polymer is preferably a water-absorbing elastomer and more preferred a water-dispersible branched polyester.

The use of branched water-dispersible polyester in adhesive agents gives the following advantages:

The adhesive agent has a superior adhesion in moist environments by effecting an immediate absorption of water, giving a better wet tack as compared to a conventional adhesive agents based on non-absorbing self-adhesive elastomers. The branched water-dispersible polyester also contributes to good adherence over a longer period of time since the stickiness of the elastomer is retained even after absorption of body fluids.

The adhesive agent is easily removed by washing due to the water-dispersibility of the polyester in tap water, but the adhesive agent is not affected by body fluids. The body fluids are ionic solutions in which the polyester component is not dispersible. Adhesive residues left on the skin can thus be removed very easily using tap water.

Suitable water-dispersible branched polyester are polyesters having the following physical properties: a Brookfield Thermosel viscosity at 177° C. of 1,000–500,000 mPa.s, more preferably 1,000–50,000 mPa.s, and most preferably of 2,000–8,000, mPa.s a ring & ball softening point of 50–150° C. more preferably of 80–90° C., a penetration hardness as determined according to ASTM D 5 of 5–50 dmm, preferably about 30 dmm and a glass transition temperature $T_g$ according to ASTM D 3418 of from 5 to −10° C., preferably about −5° C.

A reduction or even omission of the amount of hydrocoloids is rendered possible as the branched water-dispersible polyester contributes to the absorption. A reduction of the amount of hydrocolloids improves the stability of the adhesive due to the reduction of the disintegration caused by the considerable swelling of the hydrocolloids in conventional skin friendly adhesives upon absorption of body fluids.

When hydrocolloids are present, suitable hydrocolloids are naturally occurring hydrocolloids such as guar, locust bean gum (LBG), pectin, alginates, gelatine, xanthan or karaya, semisynthetic hydrocolloids such as cellulose derivatives (e.g., salts of carboxymethylcellulose, methylcellulose and hydroxypropylmethylcellulose), sodium starch glycolate and synthetic hydrocolloids such as polyvinylalcohol, polyethylene glycol or polyacrylates.

Pigments may be used as fillers or for dying the adhesives of the invention. Suitable pigments are pigments conventionally used in adhesive compositions, e.g., titanium dioxide or zinc oxide. Zinc oxide offers the advantage of showing an antibacterial effect.

Preferred adhesives to be used according to the invention are, e.g., adhesives comprising branched water-dispersible polyester and amorphous poly-alpha-olefines and having the composition:

| | |
|---|---|
| 0–10% | Ethylene/1-butene Copolymer (e.g., Hüls Vestoplast 520) |
| 20–40% | Propene/1-hexene Copolymer (e.g., Eastman Eastoflex D-127) |
| 0–10% | Triblock copolymer (e.g., SIS, such as KRATON D1107 from Shell Chemicals) |
| 0–15% | Polybutene (e.g., HYVIS 10, HYVIS 2000) |
| 0–15% | Liquid polyterpene-tackifier (e.g., Goodyear Wingtack 10) |
| 0–15% | Hydrogenated poly(hydrocarbon/terpene) tackifier (e.g., Goodyear Wingtack 95). |
| 0–15% | Optionally hydrogenated rosin acid and esters thereof |
| 0–10% | Plasticizer (e.g., dioctyl adipate) |
| 10–50% | Eastman water-dispersible branched polyester (e.g., AQ1045) |
| 0–50% | Hydrocolloids (e.g., CMC, Natrosol, Ca-alginat etc.) |
| 0–5% | Pigment, e.g., zinc oxide |

Other preferred adhesives to be used according to the invention are, e.g., adhesives comprising branched water-dispersible polyester and block copolymers and having the composition:

| | |
|---|---|
| 0–10% | Triblock copolymer (e.g., SIS) |
| 10–50% | Diblock copolymer (e.g., SI) |
| 0–10% | Plasticizer (e.g., dioctyladipate) |
| 0–15% | Tackifier (e.g., liquid polyterpene, hydrogenated poly(hydrocarbon/terpene) and or hydrogenated rosin) |
| 0–10% | Microcrystalline wax (e.g., Wax Total 40/60 from Total) |
| 10–50% | Eastman water-dispersible branched polyester (e.g., AQ1045) |
| 0–50% | Hydrocolloids (e.g., CMC, Natrosol, Ca-alginat etc.) |
| 0–5% | Pigment, e.g., zinc oxide |

Further preferred adhesives to be used according to the invention are, e.g., adhesives comprising branched water-dispersible polyester and glycerol and having the composition:

| | |
|---|---|
| 10–50% | Glycerol |
| 10–50% | Eastman water-dispersible branched polyester (e.g., AQ1045) |
| 0–50% | Hydrocolloids (e.g., CMC, Natrosol, Ca-alginat etc.) |
| 0–5% | Pigment, e.g., zinc oxide |

Yet further preferred adhesives to be used according to the invention are, e.g., adhesives comprising branched water-dispersible polyester and polyethylene glycol (PEG) and having the composition:

| | |
|---|---|
| 10–50% | Polyethylene glycol (e.g., PEG 400) |
| 10–50% | Eastman water-dispersible branched polyester (e.g., AQ1045) |
| 0–50% | Hydrocolloids (e.g., CMC, Natrosol, Ca-alginat etc.) |
| 0–5% | Pigment, e.g., zinc oxide |

The olefin component of the block-copolymers comprising styrene and one or more olefins is preferably a diene, especially a polybutadiene such as butadiene, isobutylene or isoprene.

In a preferred embodiment the sealing member has a flange stretching from the outer rim thereof. Such a flange provides extra security against leaks and excludes direct contact between the exudates and the coupling part of the ostomy device. Thus, pollution or contamination of parts of the body side member during service or exchange of the receiving member or bag is avoided. Avoidance of pollution or contamination of the body side member is of great importance when extending the weartime of the body side member as remains of the exudate on the body side member which may cause odour are avoided. The flange preferably has an adhesive on the side facing the body side member.

In another preferred embodiment, the separate sealing member disposed in the hole of the wafer or pad surrounding the stoma has overall plastic properties, wherein at least the area covering the separate sealing member is provided with a guide for adaptation of the hole of an ostomy appliance to the size of an ostomy.

It is especially preferred that the guide is visible from the side of a release liner facing the sealing member as this allows for a very simple adaptation of the hole before placing the sealing member around the stoma.

The present invention enables the user to apply an ostomy appliance without the use of any tools. Thus, it is only necessary to use body side members having a sufficiently big hole, no adaptation by cutting using scissors is necessary, and the sealing member is adapted snugly to the stoma and the body side member using the finger.

In another aspect, the invention relates to an ostomy sealing member in the form of a mouldable mass or ring which has a sufficient adhesiveness to adhere to the skin and seal around an ostomy and between the ostomy and an ostomy appliance adapted to receive secretions from the ostomy and which has a sufficient cohesion to be removed in one piece, independently of removal of the ostomy appliance, without leaving remaining adhesive on the skin or the ostomy appliance.

In a further aspect, the invention relates to an ostomy sealing member in the form of a medical grade adhesive in the form of a disc having an outer diameter corresponding to the hole in a body side ostomy member and being supplied with a pre-formed hole or for custom-adaptation or fit using a tool and/or a template.

A sealing member of the invention may be an adhesive component as disclosed above.

The sealing member of the invention may be used together with any ostomy appliance known per se for sealing between an ostomy and a body side member. This is also considered an aspect of the invention.

In yet another aspect, the invention relates to the use of a mouldable mass or ring of a hypo-allergenic, substantially non-memory putty-like adhesive as a separate sealing member to be disposed in a hole of a wafer or pad of a body side member of an ostomy appliance for securing the ostomy appliance to the user's skin, the hole receiving a stoma, and the appliance optionally comprising a separately exchangeable receiving member or bag secured to the body side ostomy member for receiving secretions from the ostomy.

In still another aspect, the invention relates to the use of a flexible and compliant hypoallergenic adhesive as a separate sealing member to be disposed in a hole of a wafer or pad of a body side member of an ostomy appliance for securing the ostomy appliance to the user's skin, the hole receiving a stoma, and the appliance optionally comprising a separately exchangeable receiving member or bag secured to the body side ostomy member for receiving secretions from the ostomy.

Such a sealing member preferably comprises a hole for receiving the stoma. When applying the sealing member, the size of the hole may be enlarged to fit to the stoma or even larger whereafter sealing is provided by pressing the sealing member to fit snugly around the stoma. In one embodiment of the invention, the hole of a sealing member is provided with incisions from the rim of the hole, preferably radially, which renders it possible also to use sealing members having some elasticity.

In yet another aspect, the invention relates to a method of applying an ostomy appliance body side member comprising an adhesive wafer or pad for securing the appliance to the user's skin, the wafer or pad having a hole for receiving a stoma and a sealing member for sealing around the stoma disposed in the hole, said sealing member having a hole for receiving the stoma, wherein the hole in the sealing member is enlarged by everting the inner rim of the hole towards or away from the stoma or by displacing the inner rim radially outwardly adapting the size of the hole of the sealing member to the size of the ostomy, aligning the stoma and the hole of the sealing member for accommodating the stoma and placing the sealing member and the body side member on the abdomen of the ostomate with the stoma projecting into the hole and moulding the sealing member to seal around the stoma.

This method allows for a simple adaptation of the ostomy appliance to the actual size of the stoma before placing the appliance around the stoma.

Materials and Methods

KRATON® G1726 from Shell: Styrene-ethylenebutylene-styrene copolymer (SEBS) having a molecular weight of 45,000 as determined by GPC and a content of diblock copolymer of 70%.

KRATON® D1118 from Shell: Styrene-butadiene-styrene copolymer (SBS) having a molecular weight of 103,000 (GPC) and a content of diblock copolymer of 80%.

VECTOR® 4114 from Exxon: Styrene-isoprene-styrene copolymer (SIS) having a molecular weight of 130,000 and a content of diblock copolymer of 40%

VISTANEX® LM-MH from Exxon: polyisobutylene (PIB) having a molecular weight of 90,000 (GPC).

Wax Total 40/60 from TOTAL

Petroleum jelly: Vaselinum Album from Witco

Polybutene oil: HYVIS® 10 from BP having a molecular weight of 1,500.

Polybutene: HYVIS® 2000 from BP having a molecular weight $M_w$ of 30,000

Mineral Oil: PL 500 from Parafluid Mineral Oil

Tackifier resin: REGALITE® R91 resin from Hercules or ARKON® P-90 resin from Arakawa Sodium carboxymethylcellulose: AKUCELL® AF2881 from Akzo or BLANOSE® 9H4XF from Hercules Corp.

Guar gum: Guar Gum FG 200 from Nordisk Gelatine

Pectin: Pektin LM 12CG Z from Copenhagen Pectin or Pektin USP/100 from Copenhagen Pectin Gelatin: Gelatine P.S.98.240.233 from ED. Geistlich Sohne AG Zinc Oxide: Zinkoxid Pharma from Hoechst AG A Z mixer Type LKB 025 from Herman-Linden was used.

AQ1045 from Eastman. A branched water-dispersible polyester.

AQ1350 from Eastman. A branched water-dispersible polyester.

KRATON® D 1107 from Shell Chemical Company. Styrene-isoprene-styrene copolymer (SIS) having a molecular weight of 212,000–260,000 as determined by GPC.

LVSI 101 from Shell Chemical Company. Styrene-isoprene-styrene diblock copolymer (SIS) having a molecular weight of 30,000 as determined by GPC Dioctyladipate from International Speciality Chemicals Ltd. A plastisizer.

METALYN 200, a methyl ester of rosin from Hercules

Eastoflex E1003, E 1060 and E 1200 from Eastman. propylene-ethylene copolymers.

Eastoflex D127 from Eastman. A propylene/1-hexene copolymer

Vestoplast 704, 708 and 750: amorphous propylene-rich poly-α-olefins from Hüls Chemie Foral 85-E from Hercules. A hydrogenated rosin.

Wingtack 10 from Goodyear. A liquid polyterpene tackyfier resin

Glycerol.

PEG 400 from Hoechst. Polyethylene glycol.

Klucel HXF EP. Hydroxypropyl cellulose.

The invention is explained more in detail in the below examples setting forth embodiments of the invention. It is clear that the embodiments may be varied without deviating from the gist of the invention and thus, the examples are not to be considered restricting the scope of the invention set forth in the appended claims.

Experimental Part

EXAMPLE 1

Preparation of a mouldable mass to be used according to the invention.

100 grams of KRATON® G1726 was used and the amounts of other ingredients used correspond to the composition stated in Table 1.

Equal amounts of KRATON® G1726 (SEBS) and of VISTANEX® LM-MH were mixed in a Z Mixer for 20 minutes at 160° C. under a vacuum of 100 mbar. Then, the vacuum was released, the mixing was continued at 160° C. for 10 minutes and the remains of VISTANEX® LM-MH, the wax, and petroleum jelly were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

The paste is then ready to use and may preferably be packed in metered amounts, e.g. in a blister pack or rod. A rod may be rolled and have a release liner on one or both sides. The product is preferably produced and packed under aseptic conditions.

EXAMPLE 2

Preparation of a mouldable mass to be used according to the invention.

100 grams of KRATON® G1726 was used and the amounts of other ingredients used correspond to the composition stated in Table 1.

Equal amounts of KRATON® G1726 (SEBS) and VISTANEX® LM-MH were mixed in a Z Mixer for 20 minutes at 160° C. under a vacuum of 100 mbar. Then, the vacuum was released, the mixing was continued at 160° C. for 10 minutes and the remains of VISTANEX® LM-MH, the wax, and HYVIS® 10 or PL 500 were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

The paste is then ready to use and may preferably be packed in metered amounts, e.g., in a blister pack or rod. A rod may be rolled and have a release liner on one or both sides. The product is preferably produced and packed under aseptic conditions.

EXAMPLES 3–5

Preparation of mouldable masses to be used according to the invention.

In the same manner as described in Example 2 above, mouldable masses according to the invention were produced having the compositions stated in the below Table 1:

TABLE 1

Composition of mouldable masses of the invention of Examples 1–5 stated in % by weight

| Component | Example 1 | Example 2 | Example 3 | Example 4 | Example 5 |
|---|---|---|---|---|---|
| SEBS | 5 | 5 | 5 | 10 | 8 |
| PIB | 30 | 15 | 15 | 10 | 18 |
| Microcrystalline wax | 5 | 5 | 5 | 5 | 5 |
| Petroleum jelly | 10 | | | | |
| Polybutene oil | | 25 | | | |
| Liquid paraffin | | | 25 | 25 | 20 |
| CMC | | | 12 | 20 | 15 |
| Guar Gum | 15 | 20 | | | |
| Pectin | 15 | 10 | 10 | 10 | 8 |
| Gelatine | 18 | 17.5 | 27 | 20 | 25 |
| Zinc white | 2 | 2.5 | 1 | | 3 |

EXAMPLE 6

Preparation of a mouldable mass to be used according to the invention.

Equal amounts of KRATON® G1726 (SEBS) and HYVIS® 2000 were mixed in a Z Mixer for 30 minutes at 160° C. under a vacuum of 100 mbar and the HYVIS® 2000 was added in four parts to ensure homogeneity during the admixing over a period of 20 minutes. Then, the remains of HYVIS® 2000 was added in four parts at 160° C. over 30 minutes and the vacuum was released. The HYVIS® 10 was added in four parts and mixed for 15 minutes. Wax was added and mixed for 10 minutes. Then, the heating was turned off, and guar gum and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. in a blister pack or rod. A rod may be rolled and have a release liner on one or both sides. The product is preferably produced and packed under aseptic conditions.

EXAMPLES 7–8

Preparation of mouldable masses to be used according to the invention.

In the same manner as described in the Example 2 above, mouldable masses according to the invention were produced having the compositions stated in the below Table 2:

TABLE 2

Composition of mouldable masses of the invention of Examples 6–8 stated in % by weight

| Component | Example 6 | Example 7 | Example 8 |
|---|---|---|---|
| SEBS (Diblock content about 70%) | 5 | | |
| SIS (Diblock content about 40%) | | 5 | |
| SB (Diblock content about 80%) | | | 5 |
| PIB | | 15 | 15 |
| Polybutene ($M_W$ 30.000) | 15 | | |
| Polybutene oil | 25 | 25 | 25 |
| Microcrystalline wax | 5 | 5 | 5 |
| CMC | 10 | 13 | 25 |
| Guar Gum | 15 | | |
| Pectin | 5 | 10 | 8 |
| Gelatine | 18 | 22 | 15 |
| Zinc white | 2 | 5 | 2 |

EXAMPLES 9–10

Preparation of mouldable masses to be used according to the invention.

Equal amounts of KRATON® G1726 (SEBS) and HYVIS® 2000 were mixed in a Z Mixer for 30 minutes at 160° C. under a vacuum of 100 mbar and the HYVIS® 2000 was added in four parts to ensure homogeneity during the admixing over a period of 20 minutes. Then, the remains of HYVIS® 2000 was added in four parts at 160° C. over 30 minutes and the vacuum was released. The HYVIS® 10 was added in four parts and mixed for 15 minutes. Resin and wax was added and mixed for 10 minutes each. Then, the heating was turned off, and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. in a blister pack or rod. A rod may be rolled and have a release liner on one or both sides. The product is preferably produced and packed under aseptic conditions.

TABLE 3

Composition of mouldable masses of the invention of Examples 9–10 stated in % by weight:

| Component | Example 9 | Example 10 |
|---|---|---|
| SEBS (Diblock content about 70%) | 5 | 5 |
| Polybutene ($M_W$ 30.000) | 10 | 5 |
| Polybutene oil | 25 | 25 |
| Resin | 5 | 10 |
| Microcrystalline wax | 5 | 5 |
| CMC | 15 | 15 |
| Pectin | 10 | 10 |
| Gelatine | 24 | 24 |
| Zinc white | 1 | 1 |

EXAMPLES 11–12

Preparation of mouldable masses to be used according to the invention.

In the same manner as described in the Example 6 above, mouldable masses according to the invention were produced having the compositions stated in the below Table 4.

TABLE 4

Composition of mouldable masses of the invention of
Examples 11–12 stated in % by weight:

| Component | Example 11 | Example 12 | Example 13 |
|---|---|---|---|
| SEBS (Diblock content about 70%) | 5 | 5 | 5 |
| Polybutene ($M_W$ 30.000) | 15 | 15 | 20 |
| Polybutene oil, HYVIS 10 or 30* | 25 | 25 | 20 |
| Amorphous polyolefin wax | 2.5 | 5 | 2.5 |
| Microcrystalline wax | 2.5 | | 2.5 |
| CMC | 20 | 20 | 20 |
| Pectin | 10 | 12 | 10.5 |
| Gelatine | 19 | 17.5 | 19 |
| Zinc white | 1 | 0.5 | 0.5 |

In Examples 11–12, HYVIS 10 was used and in Example 13, HYVIS 30 was used.

EXAMPLE 13

Preparation of a mouldable mass according to the invention.

100 grams of KRATON® G1726 was used and the amounts of other ingredients used correspond to the composition stated in Table 4.

Equal amounts of KRATON® G1726 (SEBS) and HYVIS® 2000 were mixed in a Z Mixer for 1½ hours at 160° C. under a vacuum of 100 mbar and the HYVIS® 2000 was added in four parts to ensure homogeneity during the admixing over a period of 20 minutes. Then, the remains of HYVIS® 2000 was added in four parts and wax was at 160° C. over 3 hours and the vacuum was released. Then, the heating was turned off, and HYVIS® 30 and CMC were added over 15 minutes at maximum 60° C. under a vacuum of 100 mbar and mixed for 1 hour. Finally, pectin, gelatine and zinc oxide were admixed at a temperature of 60° C. and mixed for 10 minutes.

EXAMPLES 14–19

Preparation of further adhesive compositions to be used according to the invention.

EXAMPLE 14

An adhesive agent having the composition stated in Table 5 was prepared in a Z-blade mixer. Before the mixing, the mixing chamber was heated to 140° C. by means of an oil heater. AQ1045, Eastoflex D127, Eastoflex E1003, dioctyladipate and the hydrocolloids were weighed out separately. Firstly Eastoflex D127 and E1003 were mixed for 15 minutes. AQ1045 was added and the mixing continued for 10 minutes. Dioctyladipate was added and mixed for additional 10 minutes. The heat supply was turned off and the mixing chamber was cooled down to 80° C. The hydrocolloids (a mixture of pectin, hydroxypropyl cellulose and gelatine in the ratio 1:1.5:1) were added and the mixing was continued in vacuo until a total mixing time of 60 minutes. The adhesive agent was removed from the mixer and pressed into 1 mm thin plates between two sheets of silicon paper in a hydraulic press at 90° C.

EXAMPLE 15

An adhesive agent having the composition stated in Table 5 was prepared in a Z-blade mixer. Before the mixing, the mixing chamber was heated to 140° C. by means of an oil heater. AQ1350, Eastoflex D127, Eastoflex E1003, Wingtack 10 and dioctyladipate were weighed out separately. Firstly Eastoflex D127 and E1003 were mixed for 15 minutes. AQ1350 and was added and the mixing continued for 10 minutes. Wingtack 10 was added and mixed for additional 10 minutes and finally dioctyladipate was added. The adhesive agent was removed from the mixer and pressed into 1 mm thin plates between two sheets of silicon paper in a hydraulic press at 90° C.

EXAMPLE 16

An adhesive agent having the composition stated in Table 5 was prepared in a Z-blade mixer. Before the mixing, the mixing chamber was heated to 150° C. by means of an oil heater. AQ1045, VECTOR4114, LVSI101, Foral 85-E and the hydrocolloids were weighed out separately. Firstly VECTOR 4114 was mixed at 150° C. for 15 minutes. LVSI 101 was added and the mixing continued for 15 minutes. The mixing chamber was cooled to 130° C. and Foral 85-E and AQ1045 was added and the mixing was continued for an additional 30 minutes. The heat supply was turned off and the mixing chamber was cooled down to 80° C. The hydrocolloids, a mixture of pectin and hydroxypropylcellulose in the ratio 1:1, and finally zinc oxide were added and the mixing was continued in vacuo until a total mixing time of 90 minutes. The adhesive agent was removed from the mixer and pressed into 1 mm thin plates between two sheets of silicon paper in a hydraulic press at 90° C.

EXAMPLE 17

An adhesive agent was having the composition stated in Table 5 prepared in a Z-blade mixer. Before the mixing, the mixing chamber was heated to 130° C. by means of an oil heater. AQ1045 and glycerol and the hydrocolloids were weighed out separately. Firstly AQ1045 and glycerol were mixed at 130° C. for 15 minutes. The heat supply was turned off and the mixing chamber was cooled down to 80° C. The hydrocolloids, a mixture of pectin and gelatine in the ratio 1:2, were added and the mixing continued in vacuo until a total mixing time of 40 minutes. The adhesive agent was removed from the mixer and is pressed into 1 mm thin plates between two sheets of silicon paper in a hydraulic press at 90° C.

EXAMPLE 18

An adhesive agent having the composition stated in Table 5 was prepared in a Z-blade mixer. Before the mixing, the mixing chamber was heated to 130° C. by means of an oil heater. AQ1045 and PEG 400 and the hydrocolloids were weighed out separately. Firstly AQ1045 and PEG 400 were mixed at 130° C. for 15 minutes. The heat supply was turned off and the mixing chamber was cooled down to 80° C. The hydrocolloids, a mixture of hydroxypropylcellulose and gelatine in the ratio 1:1, were added and the mixing continued in vacuo until a total mixing time of 40 minutes. The adhesive agent was removed from the mixer and pressed into 1 mm thin plates between two sheets of silicon paper in a hydraulic press at 90° C.

EXAMPLE 19

An adhesive agent having the composition stated in Table 5 was prepared in a Z-blade mixer in the same manner as described in Example 16.

TABLE 5

| Constituent | Example 14 | Example 15 | Example 16 | Example 17 | Example 18 | Example 19 |
|---|---|---|---|---|---|---|
| AQ1045 | 35 | | 30 | 50 | 40 | 32 |
| AQ 1350 | | 50 | | | | |
| LVSI 101 | | | 24 | | | 25 |
| KRATON D 1107 | | | | | | 5 |
| VECTOR 4114 | | | 5 | | | |
| Doctyladipate | 5 | 5 | | | | 8 |
| Eastoflex D127 | 15 | 15 | | | | |
| Eastoflex E1003 | 10 | 15 | | | | |
| Wingtack 10 | | 15 | | | | |
| Foral 85-E | | | 10 | | | |
| Glycerol | | | | 20 | | |
| PEG 400 | | | | | 20 | |
| BLANOSE 9H4XF | | | | | | |
| Pectin USP/100 | 10 | | 15 | 10 | | 15 |
| Klucel HXF EP | 15 | | 15 | | 20 | 15 |
| Gelatine | 10 | | | 20 | 20 | |
| Zinc oxide | | | 1 | | | |

EXAMPLES 20–24

Adhesives being suitable as pastes having the compositions stated in Table 6 were prepared in a Z-mixer in the same manner as described in Example 14.

TABLE 6

| Constituent | Example 20 | Example 21 | Example 22 | Example 23 | Example 24 |
|---|---|---|---|---|---|
| Eastoflex E 1003 | 15 | 15 | 15 | 20 | 20 |
| Eastoflex E 1060 | | | | 2.5 | 2.5 |
| AQ 1350 | 35 | 35 | 35 | 35 | 35 |
| Dioctyladipate | 5 | 5 | 5 | 5 | |
| Metalyn 200 | | | | | 5 |
| Vestoplast 708 | 10 | 5 | 5 | 2.5 | 2.5 |
| Vestoplast 704 | | 5 | 2.5 | | |
| Vestoplast 750 | 10 | | 2.5 | | |
| Gelatine | 10 | 10 | 10 | 10 | 10 |
| Pectin | 15 | 10 | 10 | 10 | 10 |
| Klucel | | 15 | 15 | 15 | 15 |

What is claimed is:

1. An ostomy appliance comprising a body side member having a coupling flange and an adhesive wafer for securing the appliance to skin, said wafer having a hole for receiving a stoma, said ostomy appliance further comprising a separate sealing member disposed in the hole of the wafer for surrounding the stoma, said sealing member having
    a) an adhesive portion of hypo-allergenic adhesive in the form of a moldable mass with an outer diameter that corresponds to the hole in the body side member and an inner diameter defining a hole, said adhesive for adhering to the skin and sealing around the stoma and for filling a void between the stoma and the body side member and having sufficient cohesion to be removed in one piece, independently of removal of the body side member when such is in use; and
    b) a backing which covers a surface of the adhesive portion and projects from the outer diameter of said adhesive portion to define a flange which prevents direct contact between exudates and the coupling flange of the body side member, said sealing member being removable separately from said body side member after said ostomy appliance has been applied to the skin.

2. The ostomy appliance as claimed in claim 1, wherein the adhesive portion of said sealing member is a substantially non-memory putty-like adhesive.

3. The ostomy appliance as claimed in claim 1, wherein the adhesive portion of said sealing member is a moldable mass having weak elasticity.

4. The ostomy appliance as claimed in claim 1, wherein the sealing member disposed in the hole of the wafer for surrounding the stoma is provided with a release liner, wherein at least an area of the release liner covering the sealing member is provided with a guide indicating a size of the hole defined by said inner diameter, said guide for use in adaptation of said ostomy appliance to the size of the stoma.

5. The ostomy appliance as claimed in claim 4, wherein the release liner is transparent.

6. The ostomy appliance as claimed in claim 1, wherein the sealing member is ring-shaped.

7. An ostomy sealing member comprising:
    a) an adhesive portion of hypo-allergenic adhesive in the form of a moldable mass having an outer diameter that corresponds to a hole in a body side ostomy member and an inner diameter defining a hole, wherein the adhesive is adapted to adhere to skin and seal around an ostomy and fill a void between the ostomy and the body side ostomy member and which has sufficient cohesion to be removed in one piece, independently of removal of the body side ostomy member when such is in use, without leaving remaining adhesive on the skin or the body side ostomy member; and
    b) a backing which covers a surface of the adhesive and extends out from the outer diameter of said adhesive portion to define a flange which prevents direct contact between exudates and a coupling flange of the body side member during use thereof.

8. The ostomy sealing member as claimed in claim 7, wherein the sealing member is ring-shaped and said adhesive portion is a substantially non-memory putty-like adhesive.

* * * * *